US009333032B2

(12) United States Patent
Prakash et al.

(10) Patent No.: US 9,333,032 B2
(45) Date of Patent: May 10, 2016

(54) MICROWAVE ANTENNA ASSEMBLY AND METHOD OF USING THE SAME

(75) Inventors: Mani N. Prakash, Boulder, CO (US); Emilie Johnson, San Francisco, CA (US); Tao Nguyen, San Jose, CA (US); Brian Shiu, Sunnyvale, CA (US)

(73) Assignee: Covidien LP, Mansfield, MA (US)

( * ) Notice: Subject to any disclaimer, the term of this patent is extended or adjusted under 35 U.S.C. 154(b) by 1044 days.

(21) Appl. No.: 13/281,605

(22) Filed: Oct. 26, 2011

(65) Prior Publication Data

US 2012/0041433 A1 Feb. 16, 2012

Related U.S. Application Data

(62) Division of application No. 11/529,823, filed on Sep. 29, 2006, now Pat. No. 8,068,921.

(51) Int. Cl.
*A61B 18/18* (2006.01)
(52) U.S. Cl.
CPC ............. *A61B 18/18* (2013.01); *A61B 18/1815* (2013.01); *A61B 2018/1807* (2013.01)
(58) Field of Classification Search
CPC ............... A61B 18/18; A61B 18/1815; A61B 2018/1807; A61B 2018/1892; A61B 2018/1853; A61B 2018/183
USPC .................................................. 607/154, 156
See application file for complete search history.

(56) References Cited

U.S. PATENT DOCUMENTS

| 2,022,065 A | 11/1935 | Wappler |
| 2,047,535 A | 7/1936 | Wappler |
| 3,330,278 A | 7/1967 | Santomieri |
| 3,351,463 A | 11/1967 | Rozner et al. |
| 3,516,412 A | 6/1970 | Ackerman |
| 3,598,108 A | 8/1971 | Jamshidi et al. |
| 3,714,851 A | 2/1973 | Orser |
| 3,753,700 A | 8/1973 | Harrison et al. |
| 3,886,944 A | 6/1975 | Jamshidi |
| 3,890,977 A | 6/1975 | Wilson |

(Continued)

FOREIGN PATENT DOCUMENTS

| EP | 0 385 604 A2 | 9/1990 |
| EP | 0 395 997 A1 | 11/1990 |

(Continued)

OTHER PUBLICATIONS

AU Examination Report for AU 2012200224, dated Nov. 29, 2013; 3 pages.

(Continued)

*Primary Examiner* — Michael Peffley

(57) ABSTRACT

A microwave antenna assembly comprising an elongate shaft having proximal and distal ends and a lumen defined therebetween, a conductive member at least partially disposed within the inner lumen of elongate shaft, conductive member being selectively deployable relative to a distal end of elongate shaft from a first condition wherein a distal end of conductive member at least partially abuts the distal end of elongate shaft to a second condition wherein the distal end of conductive member is spaced relative to the distal end of elongate shaft and a first dielectric material disposed between elongate shaft and conductive member, wherein a portion of conductive member is distal to the distal end of elongate shaft and adapted to penetrate tissue.

18 Claims, 12 Drawing Sheets

(56) References Cited

U.S. PATENT DOCUMENTS

| | | |
|---|---|---|
| 4,010,756 A | 3/1977 | DuMont et al. |
| 4,103,690 A | 8/1978 | Harris |
| 4,274,408 A | 6/1981 | Nimrod |
| 4,311,154 A | 1/1982 | Sterzer et al. |
| 4,341,226 A | 7/1982 | Peters |
| 4,402,328 A | 9/1983 | Doring |
| 4,448,198 A | 5/1984 | Turner |
| 4,557,272 A | 12/1985 | Carr |
| 4,565,200 A | 1/1986 | Cosman |
| 4,592,356 A | 6/1986 | Gutierrez |
| 4,595,007 A | 6/1986 | Mericle |
| 4,612,940 A | 9/1986 | Kasevich et al. |
| 4,616,656 A | 10/1986 | Nicholson et al. |
| 4,621,642 A | 11/1986 | Chen |
| 4,633,880 A | 1/1987 | Osypka et al. |
| 4,658,836 A | 4/1987 | Turner |
| 4,665,906 A | 5/1987 | Jervis |
| 4,682,606 A | 7/1987 | DeCaprio |
| 4,700,716 A | 10/1987 | Kasevich et al. |
| 4,776,086 A | 10/1988 | Kasevich et al. |
| 4,799,495 A | 1/1989 | Hawkins et al. |
| 4,800,899 A | 1/1989 | Elliott |
| 4,825,880 A | 5/1989 | Stauffer et al. |
| 4,869,259 A | 9/1989 | Elkins |
| 4,925,445 A | 5/1990 | Sakamoto et al. |
| 4,966,583 A | 10/1990 | Debbas |
| 5,011,473 A | 4/1991 | Gatturna |
| 5,018,530 A | 5/1991 | Rank et al. |
| 5,059,197 A | 10/1991 | Urie et al. |
| 5,067,957 A | 11/1991 | Jervis |
| 5,085,659 A | 2/1992 | Rydell |
| 5,122,136 A | 6/1992 | Guglielmi et al. |
| 5,158,084 A | 10/1992 | Ghiatas |
| 5,171,255 A | 12/1992 | Rydell |
| 5,183,463 A | 2/1993 | Debbas |
| 5,190,054 A | 3/1993 | Fetter et al. |
| 5,190,546 A | 3/1993 | Jervis |
| 5,197,482 A | 3/1993 | Rank et al. |
| 5,205,829 A | 4/1993 | Lituchy |
| 5,217,027 A | 6/1993 | Hermens |
| 5,221,269 A | 6/1993 | Miller et al. |
| 5,246,438 A | 9/1993 | Langberg |
| 5,249,585 A | 10/1993 | Turner et al. |
| 5,282,845 A | 2/1994 | Bush et al. |
| 5,300,068 A | 4/1994 | Rosar et al. |
| 5,301,682 A | 4/1994 | Debbas |
| 5,314,466 A | 5/1994 | Stern et al. |
| 5,344,441 A | 9/1994 | Gronauer |
| 5,350,419 A | 9/1994 | Bendel et al. |
| 5,353,804 A | 10/1994 | Kornberg et al. |
| 5,370,644 A | 12/1994 | Langberg |
| 5,370,675 A | 12/1994 | Edwards et al. |
| 5,405,346 A | 4/1995 | Grundy et al. |
| 5,409,004 A | 4/1995 | Sloan |
| 5,462,062 A | 10/1995 | Rubinstein et al. |
| 5,470,308 A | 11/1995 | Edwards et al. |
| 5,472,441 A | 12/1995 | Edwards et al. |
| 5,472,442 A | 12/1995 | Klicek |
| 5,486,183 A | 1/1996 | Middleman et al. |
| 5,488,958 A | 2/1996 | Topel et al. |
| 5,500,012 A | 3/1996 | Brucker et al. |
| 5,507,743 A | 4/1996 | Edwards et al. |
| 5,520,684 A | 5/1996 | Imran |
| 5,536,267 A | 7/1996 | Edwards et al. |
| 5,540,683 A | 7/1996 | Ichikawa et al. |
| 5,556,377 A | 9/1996 | Rosen et al. |
| 5,556,410 A | 9/1996 | Mittermeir et al. |
| 5,558,673 A | 9/1996 | Edwards et al. |
| 5,578,030 A | 11/1996 | Levin |
| 5,599,294 A | 2/1997 | Edwards et al. |
| 5,599,295 A | 2/1997 | Rosen et al. |
| 5,599,346 A | 2/1997 | Edwards et al. |
| 5,607,389 A | 3/1997 | Edwards et al. |
| 5,672,173 A | 9/1997 | Gough et al. |
| 5,672,174 A | 9/1997 | Gough et al. |
| 5,683,384 A | 11/1997 | Gough et al. |
| 5,685,853 A | 11/1997 | Bonnet |
| 5,700,243 A | 12/1997 | Narciso, Jr. |
| 5,709,697 A | 1/1998 | Ratcliff et al. |
| 5,720,718 A | 2/1998 | Rosen et al. |
| 5,735,847 A | 4/1998 | Gough et al. |
| 5,741,225 A | 4/1998 | Lax et al. |
| 5,749,887 A | 5/1998 | Heske et al. |
| 5,776,176 A | 7/1998 | Rudie |
| 5,794,626 A | 8/1998 | Kieturakis |
| 5,795,308 A | 8/1998 | Russin |
| 5,800,484 A | 9/1998 | Gough et al. |
| 5,800,486 A | 9/1998 | Thome et al. |
| 5,807,339 A | 9/1998 | Bostrom et al. |
| 5,810,804 A | 9/1998 | Gough et al. |
| 5,853,366 A | 12/1998 | Dowlatshahi |
| 5,855,576 A | 1/1999 | LeVeen et al. |
| 5,861,002 A | 1/1999 | Desai |
| 5,863,290 A | 1/1999 | Gough et al. |
| 5,871,523 A | 2/1999 | Fleischman et al. |
| 5,879,357 A | 3/1999 | Heaton et al. |
| 5,882,316 A | 3/1999 | Chu et al. |
| 5,897,554 A | 4/1999 | Chia et al. |
| 5,902,310 A | 5/1999 | Foerster et al. |
| 5,904,690 A | 5/1999 | Middleman et al. |
| 5,904,691 A | 5/1999 | Barnett et al. |
| 5,904,709 A | 5/1999 | Arndt et al. |
| 5,938,692 A | 8/1999 | Rudie |
| 5,941,890 A | 8/1999 | Voegele et al. |
| 5,954,655 A | 9/1999 | Hussman |
| 5,954,719 A | 9/1999 | Chen et al. |
| 5,957,969 A | 9/1999 | Warner et al. |
| 5,974,343 A | 10/1999 | Brevard et al. |
| 5,980,563 A | 11/1999 | Tu et al. |
| 5,989,265 A | 11/1999 | De La Joliniere et al. |
| 6,007,495 A | 12/1999 | Matula |
| 6,016,811 A | 1/2000 | Knopp et al. |
| 6,019,757 A | 2/2000 | Scheldrup |
| 6,022,362 A | 2/2000 | Lee et al. |
| 6,026,331 A | 2/2000 | Feldberg et al. |
| 6,027,501 A | 2/2000 | Goble et al. |
| 6,027,524 A | 2/2000 | Petit |
| 6,032,078 A | 2/2000 | Rudie |
| 6,039,735 A | 3/2000 | Greep |
| 6,050,954 A | 4/2000 | Mittermeier |
| 6,051,008 A | 4/2000 | Saadat et al. |
| 6,053,876 A | 4/2000 | Fisher |
| 6,053,925 A | 4/2000 | Barnhart |
| 6,056,744 A | 5/2000 | Edwards |
| 6,059,780 A | 5/2000 | Gough et al. |
| 6,073,051 A | 6/2000 | Sharkey et al. |
| 6,080,113 A | 6/2000 | Heneveld et al. |
| 6,080,114 A | 6/2000 | Russin |
| 6,080,150 A | 6/2000 | Gough |
| 6,097,985 A | 8/2000 | Kasevich et al. |
| 6,106,518 A | 8/2000 | Wittenberger et al. |
| 6,106,524 A | 8/2000 | Eggers et al. |
| 6,122,551 A | 9/2000 | Rudie et al. |
| 6,134,476 A | 10/2000 | Arndt et al. |
| 6,146,378 A | 11/2000 | Mikus et al. |
| 6,146,379 A | 11/2000 | Fleischman et al. |
| 6,146,657 A | 11/2000 | Unger et al. |
| 6,162,216 A | 12/2000 | Guziak et al. |
| 6,176,856 B1 | 1/2001 | Jandak et al. |
| 6,178,354 B1 | 1/2001 | Gibson |
| 6,181,970 B1 | 1/2001 | Kasevich |
| 6,217,528 B1 | 4/2001 | Koblish et al. |
| 6,223,086 B1 | 4/2001 | Carl et al. |
| 6,233,490 B1 | 5/2001 | Kasevich |
| 6,245,064 B1 | 6/2001 | Lesh et al. |
| 6,245,318 B1 | 6/2001 | Klibanov et al. |
| 6,251,128 B1 | 6/2001 | Knopp et al. |
| 6,275,738 B1 | 8/2001 | Kasevich et al. |
| 6,277,113 B1 | 8/2001 | Berube |
| 6,290,715 B1 | 9/2001 | Sharkey et al. |
| 6,306,132 B1 | 10/2001 | Moorman et al. |
| 6,308,091 B1 | 10/2001 | Avitall |
| 6,325,796 B1 * | 12/2001 | Berube et al. .......... 606/33 |
| 6,330,479 B1 | 12/2001 | Stauffer |

(56) References Cited

U.S. PATENT DOCUMENTS

| | | |
|---|---|---|
| 6,346,104 B2 | 2/2002 | Daly et al. |
| 6,347,251 B1 | 2/2002 | Deng |
| 6,355,033 B1 | 3/2002 | Moorman et al. |
| 6,405,733 B1 | 6/2002 | Fogarty et al. |
| 6,471,696 B1 | 10/2002 | Berube et al. |
| 6,496,738 B2 | 12/2002 | Carr |
| 6,514,251 B1 | 2/2003 | Ni et al. |
| 6,530,922 B2 | 3/2003 | Cosman et al. |
| 6,564,806 B1 | 5/2003 | Fogarty et al. |
| 6,569,159 B1 | 5/2003 | Edwards et al. |
| 6,582,426 B2 | 6/2003 | Moorman et al. |
| 6,652,520 B2 | 11/2003 | Moorman et al. |
| 6,663,624 B2 | 12/2003 | Edwards et al. |
| 6,685,700 B2 | 2/2004 | Behl et al. |
| 6,699,241 B2 | 3/2004 | Rappaport et al. |
| 6,722,371 B1 | 4/2004 | Fogarty et al. |
| 6,752,154 B2 | 6/2004 | Fogarty et al. |
| 6,752,767 B2 | 6/2004 | Turovskiy et al. |
| 6,878,147 B2 * | 4/2005 | Prakash et al. ............ 606/33 |
| 6,962,586 B2 | 11/2005 | Berube et al. |
| 7,160,292 B2 | 1/2007 | Moorman et al. |
| 7,160,296 B2 | 1/2007 | Pearson et al. |
| 7,195,630 B2 | 3/2007 | Ciarrocca |
| 7,220,259 B2 | 5/2007 | Harrington et al. |
| 7,226,446 B1 * | 6/2007 | Mody et al. ............ 606/33 |
| 7,228,164 B2 | 6/2007 | Fuimaono et al. |
| 7,229,438 B2 | 6/2007 | Young |
| 7,257,435 B2 | 8/2007 | Plaza |
| 7,258,690 B2 | 8/2007 | Sutton et al. |
| 7,261,711 B2 | 8/2007 | Mulier et al. |
| 7,261,712 B2 | 8/2007 | Burbank et al. |
| 7,267,683 B2 | 9/2007 | Sharkey et al. |
| 7,276,064 B2 | 10/2007 | Paul et al. |
| 7,282,051 B2 | 10/2007 | Rioux et al. |
| 7,282,061 B2 | 10/2007 | Sharkey et al. |
| 7,285,119 B2 | 10/2007 | Stewart et al. |
| 7,294,125 B2 | 11/2007 | Phalen et al. |
| 7,306,591 B2 | 12/2007 | Thomas et al. |
| 7,306,595 B2 | 12/2007 | Ostrovsky et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,326,201 B2 | 2/2008 | Fjield et al. |
| 7,326,208 B2 | 2/2008 | Vanney et al. |
| 7,329,253 B2 | 2/2008 | Brounstein et al. |
| 7,331,959 B2 | 2/2008 | Cao et al. |
| 7,331,960 B2 | 2/2008 | Schaer |
| 7,335,196 B2 | 2/2008 | Swanson et al. |
| 7,335,197 B2 | 2/2008 | Sage et al. |
| 7,335,198 B2 | 2/2008 | Eggers et al. |
| 2001/0001819 A1 | 5/2001 | Lee et al. |
| 2001/0037812 A1 | 11/2001 | Dobak, III et al. |
| 2001/0051131 A1 | 12/2001 | Unger |
| 2002/0022832 A1 | 2/2002 | Mikus et al. |
| 2002/0059938 A1 | 5/2002 | Fogarty et al. |
| 2002/0072742 A1 | 6/2002 | Schaefer et al. |
| 2002/0087151 A1 | 7/2002 | Mody et al. |
| 2002/0133148 A1 | 9/2002 | Daniel et al. |
| 2002/0147444 A1 | 10/2002 | Shah et al. |
| 2002/0198520 A1 | 12/2002 | Coen et al. |
| 2003/0004506 A1 | 1/2003 | Messing |
| 2003/0065317 A1 | 4/2003 | Rudie et al. |
| 2003/0069578 A1 | 4/2003 | Hall et al. |
| 2003/0088242 A1 | 5/2003 | Prakash et al. |
| 2003/0109862 A1 | 6/2003 | Prakash et al. |
| 2003/0195499 A1 * | 10/2003 | Prakash et al. ............ 606/33 |
| 2003/0195500 A1 | 10/2003 | Moorman et al. |
| 2003/0208199 A1 | 11/2003 | Keane |
| 2004/0168692 A1 | 9/2004 | Fogarty et al. |
| 2004/0225286 A1 | 11/2004 | Elliott |
| 2004/0267156 A1 | 12/2004 | Turovskiy et al. |
| 2005/0062666 A1 | 3/2005 | Prakash et al. |
| 2005/0070895 A1 | 3/2005 | Ryan et al. |
| 2005/0085881 A1 | 4/2005 | Prakash et al. |
| 2005/0149010 A1 * | 7/2005 | Turovskiy et al. ............ 606/33 |
| 2006/0217702 A1 | 9/2006 | Young |
| 2007/0049921 A1 | 3/2007 | Konishi et al. |
| 2007/0100405 A1 | 5/2007 | Thompson et al. |
| 2007/0118110 A1 | 5/2007 | Girard et al. |
| 2007/0129710 A1 | 6/2007 | Rudko et al. |
| 2007/0129721 A1 | 6/2007 | Phan et al. |
| 2007/0135700 A1 | 6/2007 | Taimisto et al. |
| 2007/0149963 A1 | 6/2007 | Matsukuma et al. |
| 2007/0149966 A1 | 6/2007 | Dahla et al. |
| 2007/0161977 A1 | 7/2007 | Moorman et al. |
| 2007/0179491 A1 | 8/2007 | Kratoska et al. |
| 2007/0179494 A1 | 8/2007 | Faure |
| 2007/0179496 A1 | 8/2007 | Swoyer et al. |
| 2007/0185483 A1 | 8/2007 | Butty et al. |
| 2007/0198006 A1 | 8/2007 | Prakash et al. |
| 2007/0203480 A1 | 8/2007 | Mody et al. |
| 2007/0203486 A1 | 8/2007 | Young |
| 2007/0219546 A1 | 9/2007 | Mody et al. |
| 2007/0232871 A1 | 10/2007 | Sinofsky et al. |
| 2007/0260234 A1 | 11/2007 | McCullagh et al. |
| 2007/0265609 A1 | 11/2007 | Thapliyal et al. |
| 2007/0265610 A1 | 11/2007 | Thapliyal et al. |
| 2007/0270789 A1 | 11/2007 | Berger |
| 2007/0270794 A1 | 11/2007 | Anderson et al. |
| 2007/0287996 A1 | 12/2007 | Rioux |
| 2007/0287999 A1 | 12/2007 | Malecki et al. |
| 2007/0293856 A1 | 12/2007 | Paul et al. |
| 2007/0299434 A1 | 12/2007 | Malecki et al. |
| 2007/0299435 A1 | 12/2007 | Crowe et al. |
| 2008/0004615 A1 | 1/2008 | Woloszko et al. |

FOREIGN PATENT DOCUMENTS

| | | |
|---|---|---|
| EP | 0 481 685 A1 | 4/1992 |
| EP | 0 667 126 A1 | 8/1995 |
| EP | 0 829 232 A2 | 3/1998 |
| EP | 0 908 154 A1 | 4/1999 |
| EP | 0 908 156 A1 | 4/1999 |
| EP | 1 559 377 A1 | 8/2005 |
| WO | WO 88/06864 A1 | 9/1988 |
| WO | WO 92/12678 A1 | 8/1992 |
| WO | WO 93/20767 A1 | 10/1993 |
| WO | WO 93/20768 A1 | 10/1993 |
| WO | WO 96/27328 A1 | 9/1996 |
| WO | WO 96/34571 A1 | 11/1996 |
| WO | WO 97/48449 A1 | 12/1997 |
| WO | WO 97/48450 A1 | 12/1997 |
| WO | WO 97/48451 A1 | 12/1997 |
| WO | WO 98/06341 A1 | 2/1998 |
| WO | WO 98/30160 A1 | 7/1998 |
| WO | WO 99/04704 A2 | 2/1999 |
| WO | WO 99/25248 A1 | 5/1999 |
| WO | WO 99/43268 A1 | 9/1999 |
| WO | WO 99/44506 A1 | 9/1999 |
| WO | WO 99/56642 A1 | 11/1999 |
| WO | WO 99/56643 A1 | 11/1999 |
| WO | WO 99/56812 A2 | 11/1999 |
| WO | WO 99/58065 A1 | 11/1999 |
| WO | WO 99/66834 A1 | 12/1999 |
| WO | WO 00/10471 A1 | 3/2000 |
| WO | WO 00/12009 A2 | 3/2000 |
| WO | WO 00/12010 A1 | 3/2000 |
| WO | WO 00/13602 A2 | 3/2000 |
| WO | WO 00/16697 A2 | 3/2000 |
| WO | WO 00/24320 A1 | 5/2000 |
| WO | WO 00/28913 A1 | 5/2000 |
| WO | WO 00/30531 A1 | 6/2000 |
| WO | WO 00/33743 A1 | 6/2000 |
| WO | WO 00/49957 A1 | 8/2000 |
| WO | WO 00/56239 A1 | 9/2000 |
| WO | WO 00/57811 A1 | 10/2000 |
| WO | WO 01/00114 A1 | 1/2001 |
| WO | WO 01/05317 A1 | 1/2001 |
| WO | WO 01/05320 A1 | 1/2001 |
| WO | WO 01/60235 A2 | 8/2001 |
| WO | WO 03/034932 A1 | 5/2003 |
| WO | WO 03/039385 A2 | 5/2003 |

(56) References Cited

FOREIGN PATENT DOCUMENTS

| WO | WO 03/088806 A2 | 10/2003 |
|---|---|---|
| WO | WO 03/088858 A1 | 10/2003 |
| WO | WO 2005/011049 A2 | 2/2005 |

OTHER PUBLICATIONS

Anonymous. (1987). Homer Mammalok ® *Breast Lesion Needle/Wire Localizer, Namic ® Angiographic Systems Division*, Glens Falls, New York, (Hospital products price list), 2 pages.

Anonymous. (1999). *Auto Suture MIBB Site Marker: Single Use Clip Applier, United States Surgical* (Product instructions), 2 pages.

Anonymous. (1999). *MIBB Site Marker, United States Surgical* (Sales brochure), 4 pages.

Anonymous. (2001). *Disposable Chiba Biopsy Needles and Trays, Biopsy and Special Purpose Needles Cook Diagnostic and Interventional Products Catalog* (Products list), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

Chou, C.K. (1995). "Radiofrequency Hyperthermia in Cancer Therapy," Chapter 94 *In Biologic Effects of Nonionizing Electromagnetic Fields*. CRC Press, Inc. pp. 1424-1428.

Gennari, R. et al. (Jun. 2000). "Use of Technetium-99m-Labeled Colloid Albumin for Preoperative and Intraoperative Localization of Nonpalpable Breast Lesions," *J. Am. Coll. Surg.* 190(6):692-699.

Kopans, D.B. et al. (Nov. 1985). "Spring Hookwire Breast Lesion Localizer: Use with Rigid-Compression. Mammographic Systems," *Radiology* 157(2):537-538.

Midtech product literature. (Mar. 2000). "D Wire": product description, one page.

Midtech product literature. (Dec. 1999). "FlexStrand": product description, one page.

Mullan, B.F. et al. (May 1999). "Lung Nodules: Improved Wire for CT-Guided Localization," *Radiology* 211:561-565.

Urologix, Inc.-Medical Professionals: Targis™ Technology (Date Unknown). "Overcoming the Challenge" located at: <http://www.urologix.com/medical/technology.html > last visited on Apr. 27, 2001. Three pages.

Urrutia et al. (1988). "Retractable-Barb Needle for Breast Lesion Localization: Use in 60 Cases," *Radiology* 169(3):845-847.

Joseph G. Andriole, M.D., et al., "Biopsy Needle Characteristics Assessed in the Laboratory", Radiology 148: 659-662, Sep. 1983.

T. Matsukawa, et al. "Percutaneous Microwave Coagulation Therapy in Liver Tumors", Acta Radiologica vol. 38, pp. 410-415, 1997.

C.F. Gottlieb, et al. "Interstitial Microwave Hyperthermia Applicators having Submillimetre Diameters", Int. J. Hyperthermia, vol. 6, No. 3, pp. 707-714, 1990.

Sylvain Labonte, et al., "Monopole Antennas for Microwave Catheter Ablation", IEEE Trans. On Microwave Theory and Techniques, vol. 44, No. 10, pp. 1832-1840, Oct. 1995.

P.R. Stauffer et al., "Interstitial Heating Technologies", Thermoradiotheray and Thermochemotherapy (1995) vol. I, Biology, Physiology, Physics, pp. 279-320.

Magdy F. Iskander, et al., "Design Optimization of Interstitial Antennas", IEEE Transactions on Biomedical Engineering, vol. 36, No. 2, Feb. 1989, pp. 238-246.

C.H. Durney, et al., "Antennas for Medical Applications", Antenna Handbook: Theory Application and Design, p. 24-40, Van Nostrand Reinhold, 1988 New York, V.T. Lo, S.W. Lee.

Murakami, R. et al., (1995). "Treatment of Hepatocellular Carcinoma: Value of Percutaneous Microwave Coagulation," American Journal of Radiology (AJR) 164:1159-1164.

Seki, T. et al., (1994). "Ultrasonically Guided Percutaneous Microwave Coagulation Therapy for Small Hepatocellular Carcinoma," Cancer 74(3): 817-825.

International Search Report for patent application No. EP 03 72 1482 dated Feb. 6, 2006.

International Search Report for International Application No. PCT/US03/09483 dated Aug. 13, 2003.

International Search Report for International Application No. EP 07 01 8821 dated Jan. 14, 2008.

\* cited by examiner

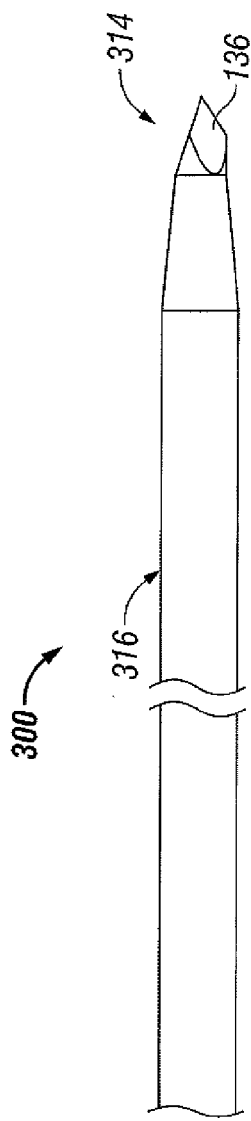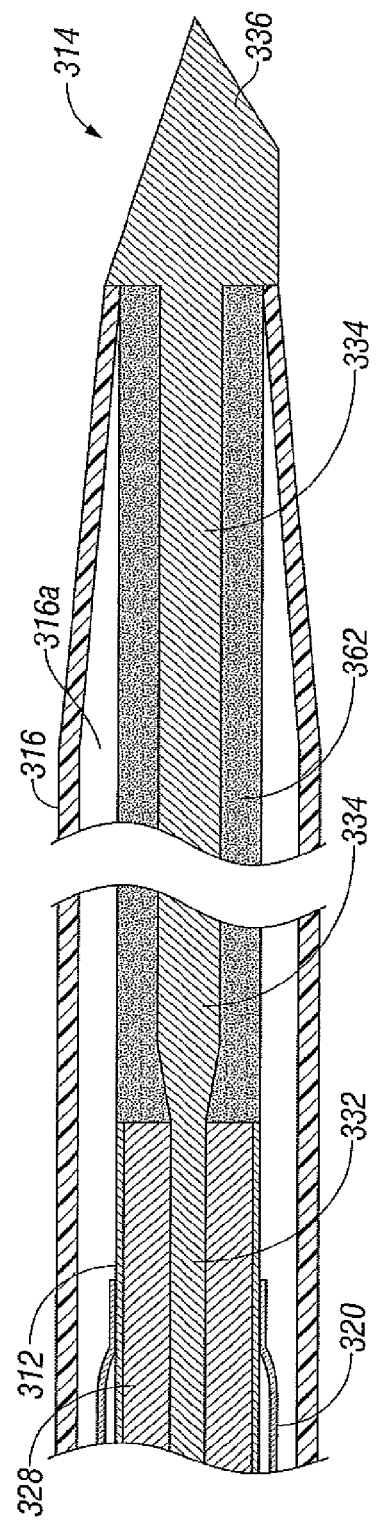

MICROWAVE ANTENNA ASSEMBLY AND METHOD OF USING THE SAME

CROSS-REFERENCE TO RELATED APPLICATIONS

This application is a divisional of U.S. patent application Ser. No. 11/529,823, filed Sep. 29, 2006, now U.S. Pat. No. 8,068,921, and entitled "Microwave Antenna Assembly and Method of Using the Same," the entire disclosure of which is hereby incorporated herein by reference in its entirety.

BACKGROUND

1. Technical Field

The present disclosure relates generally to medical/surgical ablation assemblies and methods of their use. More particularly, the present disclosure relates to microwave antenna assemblies configured for direct insertion into tissue for diagnosis and treatment of the tissue and methods of using the same.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control. This is partly why a more direct and precise method of applying microwave radiation has been sought.

Presently, there are several types of microwave probes in use, e.g., monopole, dipole, and helical. One type is a monopole antenna probe, which consists of a single, elongated microwave conductor exposed at the end of the probe. The probe is sometimes surrounded by a dielectric sleeve. The second type of microwave probe commonly used is a dipole antenna, which consists of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

SUMMARY

The present disclosure describes a device structurally robust for direct insertion into tissue, without the need for additional introducers or catheters, while in a first condition, and device, in a second condition, forms a microwave antenna capable of producing a controllable and predictable heating pattern in a clearly defined area or volume of ablation.

The present disclosure relates generally to microwave antenna assemblies and methods of their use, e.g., in tissue ablation applications. More particularly, the present disclosure relates to microwave antenna assemblies configured for direct insertion into tissue for diagnosis and treatment of the tissue and methods of using the same.

A microwave antenna assembly of the present disclosure comprises an elongate shaft having proximal and distal ends and an inner lumen defined therebetween, a conductive member at least partially disposed within the inner lumen of elongate shaft, conductive member being selectively deployable relative to a distal end of elongate shaft from a first condition wherein a distal end of the conductive member at least partially abuts the distal end of elongate shaft to a second condition wherein the distal end of conductive member is spaced relative to the distal end of elongate shaft, and a first dielectric material disposed between elongate shaft and conductive member wherein a portion of conductive member is distal to the distal end of elongate shaft and adapted to penetrate tissue.

In yet another embodiment of the present disclosure, microwave antenna assembly comprises an elongate shaft having a lumen defined therein, a conductive member partially disposed within the lumen of elongate shaft wherein conductive member including a geometry at a distal end thereof configured to penetrate tissue, a first dielectric material disposed between elongate shaft and at least a portion of conductive member and a second dielectric material which covers at least a portion of conductive member wherein at least one of elongate shaft, conductive member, first dielectric material the second dielectric material being configured to selectively deploy relative to a distal end of an introducer from a first condition wherein a distal end of conductive member at least partially abuts a distal end of introducer to a second condition wherein the distal end of conductive member is spaced relative to the distal end of introducer.

In yet another embodiment of the present disclosure, a method for deploying a microwave antenna assembly comprising the steps of advancing a microwave antenna assembly in a first condition to a region of tissue to be treated whereby a distal portion of microwave antenna assembly defines a pathway through the tissue during penetration, deploying the distal portion of microwave electrosurgical energy delivery apparatus to a second condition whereby the deployed distal portion of the microwave antenna assembly biases to a predetermined configuration, treating the region of tissue with electrosurgical energy, retracting the deployed distal portion of microwave antenna assembly to the first condition and withdrawing microwave antenna assembly from tissue.

BRIEF DESCRIPTION OF THE DRAWINGS

FIG. 18 is a side elevation view of a distal portion of a microwave assembly according to a further embodiment of the present disclosure, shown in a first condition;

FIG. 19 is an enlarged longitudinal cross-section view of the distal portion of the microwave antenna assembly of FIG. 18.

DETAILED DESCRIPTION

Figure 1:
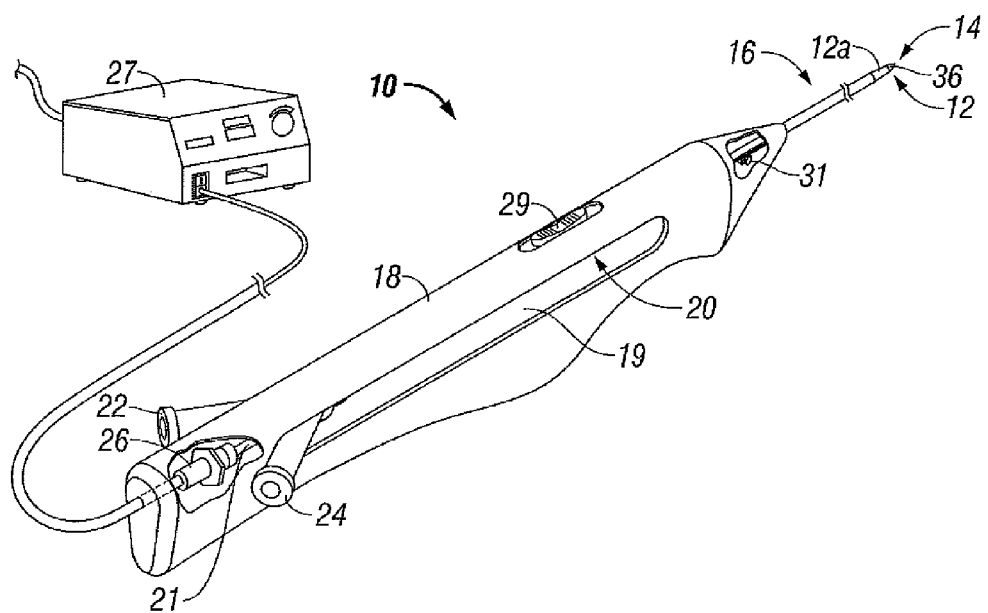
FIG. 1 is a perspective view of a microwave antenna assembly according to an embodiment of the present disclosure shown in a first condition.

Embodiments of the presently disclosed microwave antenna assembly will now be described in detail with reference to the drawing figures wherein like reference numerals identify similar or identical elements. As used herein and as is traditional, the term "distal" refers to the portion which is furthest from the user and the term "proximal" refers to the portion that is closest to the user. In addition, terms such as "above", "below", "forward", "rearward", etc. refer to the orientation of the figures or the direction of components and are simply used for convenience of description.

During invasive treatment of diseased areas of tissue in a patient the insertion and placement of an electrosurgical energy delivery apparatus, such as a microwave antenna assembly, relative to the diseased area of tissue is critical for successful treatment. Generally, assemblies described herein allow for direct insertion into tissue while in a first condition followed by deployment of the distal penetrating portion thereof to a second condition, thereby forming a microwave antenna at the distal end of the assembly for delivery of microwave electrosurgical energy. An assembly that functions similarly may be found in U.S. Patent Application Publication No. 2003/0195499 A1, filed Oct. 15, 2002, which is herein incorporated by reference.

Referring now to FIGS. 1-7, a microwave antenna assembly, according to an embodiment of the present disclosure, is shown as 10. The microwave antenna assembly 10 includes an introducer 16 having an elongate shaft 12 and a conductive member 14 slidably disposed within elongate shaft 12, a cooling assembly 20 having a cooling sheath 21, a cooling fluid supply 22 and a cooling fluid return 24, and an electrosurgical energy connector 26.

Connector 26 is configured to connect the assembly 10 to an electrosurgical power generating source 27, e.g., a generator or source of radio frequency energy and/or microwave energy, and supplies electrosurgical energy to the distal portion of the microwave antenna assembly 10. During initial insertion into tissue, while in the first condition, assembly 10 defines a path through the tissue by virtue of the mechanical geometry of the distal portion of the conductive member 14 and, if needed, by the application of energy to tissue, e.g. electrical, mechanical or electro-mechanical energy.

Figure 2:
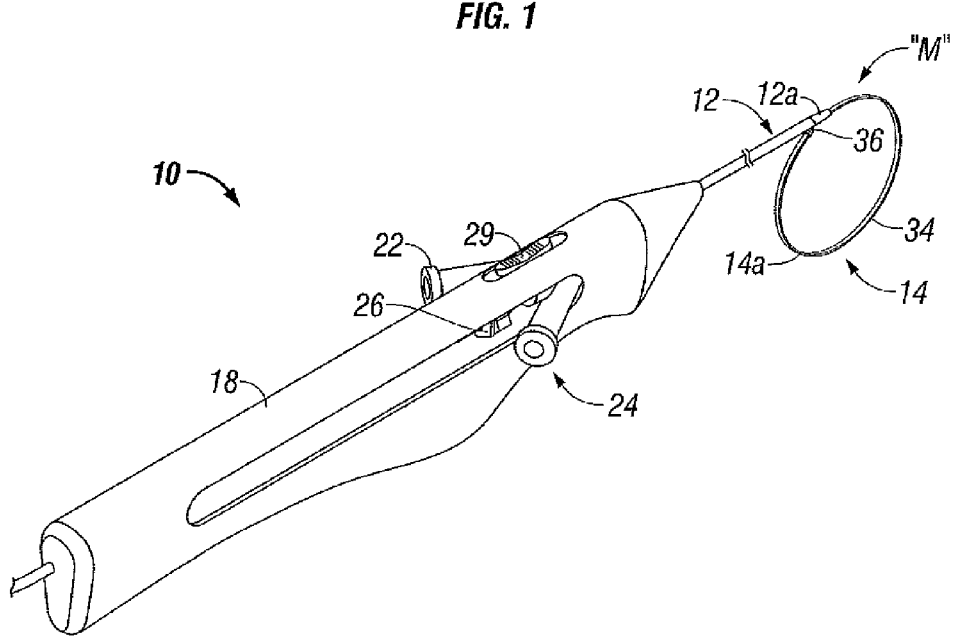
FIG. 2 is a perspective view of the microwave antenna assembly of FIG. 1, shown in a second condition.
Figure 16:
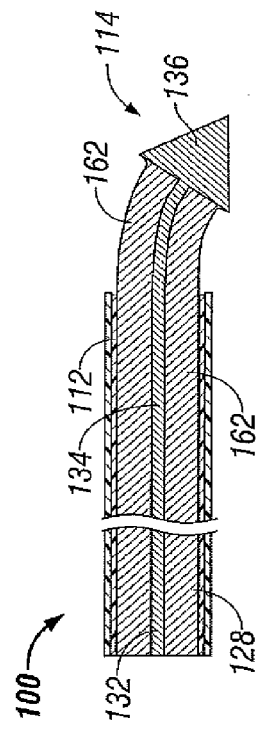
FIG. 16 is a plan view of a portion of the conductive member according to an embodiment of the present disclosure.
Figure 14:
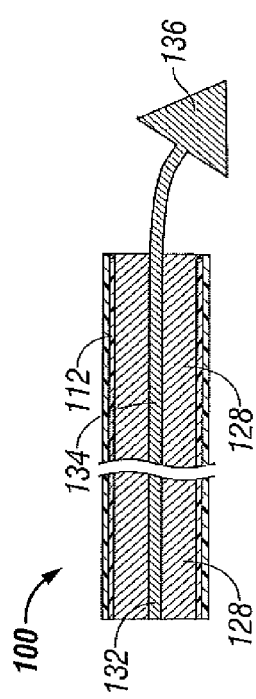
FIG. 14 is an elevational view of a portion of a conductive member according to an embodiment of the present disclosure.

As seen in FIGS. 1 and 2, microwave antenna assembly 10 includes a first condition in which conductive member 14 is in a first position substantially entirely within elongate shaft 12 and at least one second condition in which conductive member 14 is at least at a second position extended from elongate shaft 12. While in the first condition, a distal end or tip 14a of conductive member 14 is positioned beyond a distal end 12a of elongate shaft 12. While in the second condition, distal end 14a of conductive member 14 is spaced a distance relative to distal end 12a of elongate shaft 12. Second condition, as applied in the present disclosure, is any position, configuration or condition, wherein the distal end 14a of conductive member 14 is not in the first condition, e.g., distal end 14a of conductive member 14 is spaced a distance relative to distal end 12a of elongate shaft 12. For example, as illustrated in FIG. 2, conductive member may be biased to a substantially pre-determined configuration or, as illustrated in FIGS. 14 and 16, a portion of the conductive member may be biased to a pre-determined configuration. During deployment or retraction of conductive member 14, between the first condition and the second condition, distal end 14a of the conductive member 14 defines a path through the tissue by virtue of the mechanical geometry of the distal portion thereof and/or the application of energy to tissue, e.g. electrical, thermal mechanical or electro-mechanical energy.

Elongate shaft 12 and conductive member 14 are configured as a coaxial cable, in electro-mechanical communication with connector 26, which is capable of delivering electrosurgical energy. Conductive member 14 is capable of delivering radio frequency energy in either a bipolar or monopolar mode. Radio frequency energy can be delivered while microwave antenna assembly 10 is in the first or second condition. Deployment of conductive member 14 to the second condition, as illustrated in FIG. 2, forms a microwave antenna "M" at the distal end of microwave antenna assembly 10 capable of delivering microwave energy to a target tissue.

Elongate shaft 12 may be formed from a flexible, semi-rigid or rigid microwave conductive cable with the original inner conductor removed and replaced with conductive member 14. Elongate shaft 12 and conductive member 14 may be formed of suitable conductive material including and not limited to copper, gold, silver or other conductive metals having similar conductivity values. Alternatively, elongate shaft 12 and/or conductive member 14 may be constructed from stainless steel or may be plated with other materials, e.g., other conductive materials, such as gold or silver, to improve their respective properties, e.g., to improve conductivity, decrease energy loss, etc.

As seen in FIGS. 2-4A, conductive member 14 includes a proximal portion 32, a biased distal portion 34, and a distal tip portion 36. The various portions 32, 34, 36 of conductive member 14 may be constructed of one or more individual elements joined together or may be constructed from a single monolithic element. Conductive member 14 may be constructed from suitable materials exhibiting good shape memory properties, such as, for example, nitinol and stainless steel. Conductive member 14 may be partially or fully plated with a suitable material, such as gold or silver, in order to further increase the electrical conductivity thereof.

When microwave antenna assembly 10 is in the first condition, as shown in FIG. 1, at least a portion of distal tip portion 36 is disposed distal of elongate shaft 12 and introducer 16 concomitantly therewith, proximal portion 32 and biased distal portion 34 of conductive member 14 are partially disposed within inner lumen of elongate shaft 12 or inner lumen of introducer 16 and are capable of conducting radio frequency energy to distal tip portion 36. When microwave antenna assembly 10 is in the second condition, as shown in FIG. 2, proximal portion 32 of conductive member 14 is partially disposed within the inner lumen of elongate shaft 12 or the inner lumen of introducer 16. In the second condition, biased distal portion 34 and distal tip portion 36 of conductive member 14 in conjunction with the distal end of the coaxial transmission line (not shown) form a microwave antenna capable of delivering microwave energy to the target tissue. Proximal portion 32 forms an inner conductor of a coaxial transmission line and elongate shaft 12 forms an outer conductor of the coaxial transmission line. Adjustments to the dimension and diameter of proximal portion 32 and elongate shaft 12, as well as the type of dielectric material used to separate proximal portion 32 and elongate shaft 12, can be made to maintain proper impedance.

Figure 4:
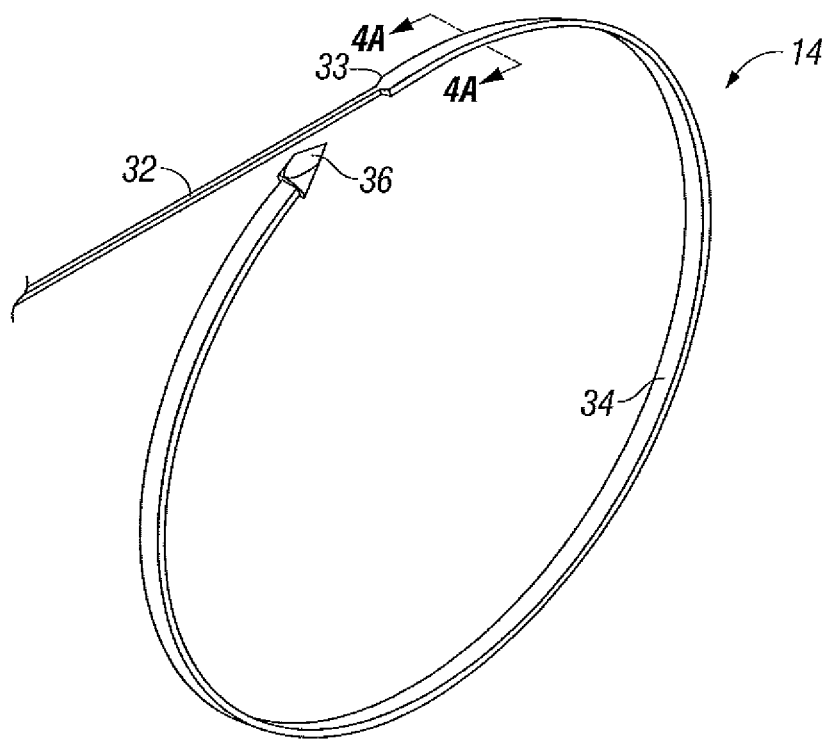
FIG. 4 is an enlarged perspective view of the indicated area of detail of FIG. 3.

When microwave antenna assembly 10 is in a retracted or first condition, as seen in FIG. 1, biased distal portion 34 is disposed within and/or constrained by elongate shaft 12 or introducer 16. When microwave antenna assembly 10 is in a deployed or second condition, as seen in FIG. 4, biased distal portion 34 deflects to a pre-determined configuration. The pre-determined configuration may be one of a variety of shapes so long as distal portion 34 substantially encloses a defined area, i.e., the shape surrounds at least a portion or majority of the target tissue. Accordingly, when deployed or in the second condition, biased distal portion 34 deflects to a suitable pre-determined configuration, such as, for example, circles, ellipses, spirals, helixes, squares, rectangles, triangles, etc., various other polygonal or smooth shapes, and partial forms of the various shapes so long as a portion or majority of the target tissue is surrounded.

Figure 4A:
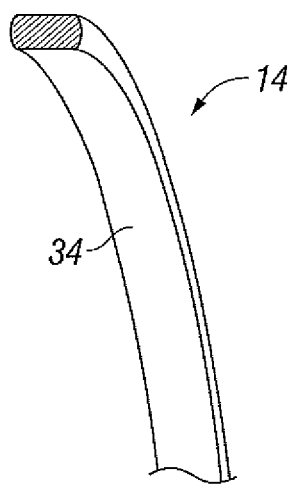
FIG. 4A is a cross-sectional view as taken through 4A-4A of the biased distal portion of the conductive member of FIG. 4.

The cross-sectional profile of biased distal portion 34 can be different from the cross-sectional profile of the other portions of conductive member 14. As seen in FIG. 4A, biased distal portion 34 of conductive member 14 may have an oblong cross-sectional profile; however, other suitable cross-sectional profiles, e.g. round, oval, square, etc. are contemplated. The shape and dimension of distal portion 34 may influence the microwave matching properties and the ability of the microwave antenna to deliver energy. The cross-sectional profile in the distal portion 34 may vary along its length to suitably match the antenna to the target tissue. Mechanically, different cross-sectional profiles may aid in the deployment of microwave antenna assembly 10 as desired and may aid in the ability of distal portion 34 to form the pre-determined configuration.

Referring again to FIG. 4, distal tip portion 36 is positioned on biased distal portion 34 of conductive member 14. The geometry of distal tip portion 36 is configured to define a pathway through the tissue during tissue penetration. The geometry of distal tip portion 36, will be discussed in the various embodiments hereinbelow.

Relatively smooth transitions between the various portions of conductive member 14 are made to avoid stress concentrators and to facilitate tissue penetration during insertion, deployment and retraction. As seen in FIG. 4, a transition 33 between proximal portion 32 and biased distal portion 34 is tapered in order to strengthen the transition and to avoid any stress points. Tapered transition 33 also aids in forming a return pathway for conductive member 14 during retraction. Other methods may also be used to strengthen the joint if multiple pieces are used.

Figure 3:
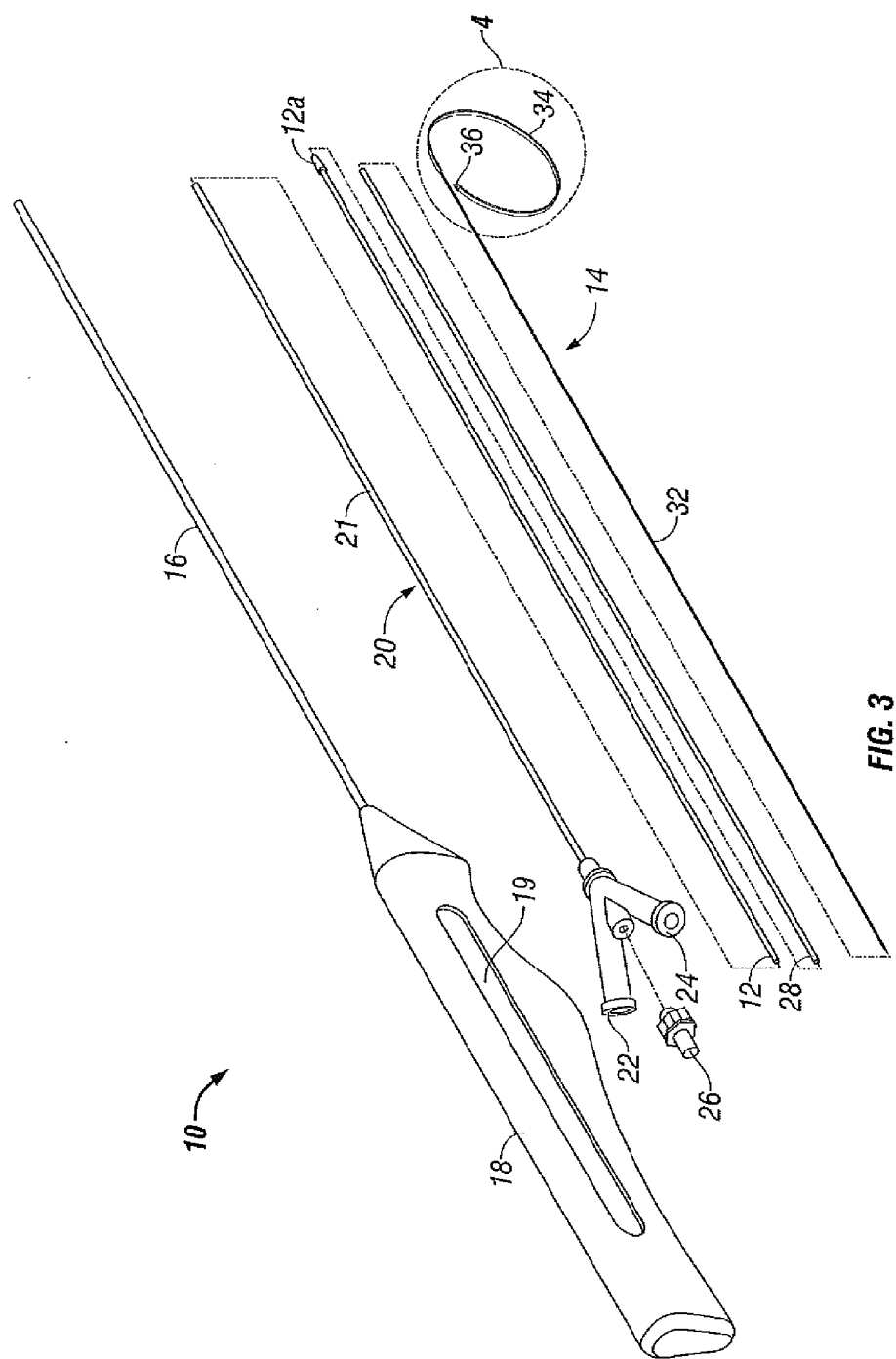
FIG. 3 is an exploded perspective view of the microwave antenna assembly of FIGS. 1 and 2.

As seen in FIG. 3, a first dielectric 28 is preferably disposed between at least a portion of elongate shaft 12 and conductive member 14 to provide insulation therebetween. First dielectric material 28 may be substantially disposed on the proximal portion 32 of conductive member 14 and may be slidably disposed within elongate shaft 12 or the position of first dielectric 28 may be fixed relative to elongate shaft 12 with the conductive member 14 slidably disposed with first dielectric 28. First dielectric material 28 may constitute any number of appropriate materials, including air. The placement and configuration of first dielectric material 28 relative to conductive member 14 is discussed in additional embodiments hereinbelow.

With continued reference to FIGS. 1-3, cooling assembly 20 surrounds elongate shaft 12 and forms a water-tight seal therewith. Cooling assembly 20 includes an elongate cooling sheath 21 configured to co-axially extend over elongate shaft 12, a cooling fluid supply 22 fluidly connected to cooling sheath 21, and a cooling fluid return 24, fluidly connected to cooling sheath 21. In operation, as will be discussed in greater detail below, cooling fluid enters cooling sheath 21 though cooling fluid supply 22 and is delivered to a distal end of cooling sheath 21 through one or more thin wall polyimide tubes (not explicitly shown) disposed within an inner lumen of cooling sheath 21. Additionally, cooling fluid flows away from the distal end of cooling sheath 21 to a proximal end thereof, absorbs energy, and exits through cooling fluid return 24.

As seen in FIGS. 1-3, handle 18 is configured to provide a gripping mechanism for the clinician, an interface for various controls and connectors for the microwave antenna assembly 10. Handle 18 defines an access slot 19 that is configured to provide access to connector 26, cooling fluid supply 22 and cooling fluid return 24. A selector 29, positioned on the proximal end of handle 18, connects to the electrosurgical energy delivery source 27. Selector 29 provides a means for the clinician to select the energy type, e.g., radio frequency or microwave, the energy delivery mode, e.g., bipolar, monopolar, and the mode of operation, e.g., manual delivery or automatic delivery during deployment from a first to a second condition.

Introducer 16, secured to the distal end of handle 18, is slightly larger than elongate shaft 12. The increased gauge size provides added strength and rigidity to the microwave antenna assembly for direct insertion into tissue. A distal portion of introducer 16 may be tapered to create a smooth transition between introducer 16 and adjacent components of the microwave antenna assembly 10. At least a portion of introducer 16 may be in direct contact with elongate shaft 12.

Deployment of the microwave antenna assembly 10 from the first condition, as seen in FIG. 1, to a second condition, as seen in FIG. 2, is accomplished by repositioning a slidable portion of the microwave antenna assembly 10 relative to a fixed portion of the microwave antenna assembly 10. In the embodiment in FIGS. 1 and 2, the slidable portion includes conductive member 14, cooling assembly 20 and connector 26, and the fixed portion includes the elongate shaft 12, introducer 16 and handle 18.

In one embodiment, to deploy the microwave antenna assembly 10 from the first condition to the second condition, a clinician grasps a portion of the fixed portion, for example, the handle, and repositions or slides the slidable portion distally until deployed to the second condition. Similarly, the clinician retracts the microwave antenna assembly 10 from the second condition to the first condition by grasping the fixed portion and repositioning or sliding the slidable portion proximally until retracted to the second condition.

Handle 18 may maintain the position of the slidable portion relative to introducer 16 and/or elongate shaft 12. As seen in FIGS. 1 and 2, cooling fluid supply 22 and cooling fluid return 24 may be restrained by the access slot 19, formed in the handle 18, thereby limiting lateral movement of the slidable portion during deployment and retraction. Guide slots (not shown), in the cooling fluid supply 22 and cooling fluid return 24, may provide a track adjacent access slot 19 that further restricts lateral movement of the slidable portion and the fixed portion during deployment and retraction. Various other suitable may be used for ensuring alignment between the slidable portion and the fixed portion.

Microwave antenna assembly may include a motorized means for controlling the position of the slidable portion. Motorized means mechanically engages at least a portion of the slidable portion and drives the slidable portion distally to deploy and proximally to retract. Delivery of radio frequency energy during deployment may coincide with position change of the slidable portion by the motorized means.

Returning to FIGS. 1-2, an embodiment of the microwave antenna assembly 10 may include a position determining means 31, such as a suitable sensor, for determining the position of distal tip portion 36 of conductive member 14. Position determining means 31 may include mechanical, magnetic, electrical or electro-mechanical means to provide feedback indicative of the position of distal tip portion 36. Positioning determining means 31 may mechanical engage a portion of a slidable portion or may electrically sense movement of the slidable portion relative to the positioning determining means 31. Alternatively, electrosurgical power generating source 27 may include electrical elements or circuitry configured to determine the presence of resistive, capacitive and/or inductive contact between conductive member 14 and elongate shaft 12 or introducer 16, indicating deployment of conductive member 14 in a second condition.

In yet another embodiment of the present invention, position determining means 31 and motorized means for positioning the slidable portion may be combined into a single device such as a micro-servo drive or similar motorized means with position control.

Other more sophisticated means may be employed for determining the position of the slidable portion, such as measuring the reflected power, or $S_{11}$, on either conductive member 14 or elongate shaft 12. Alternatively, the reflective power between conductive member 14 and elongate shaft 12, or $S_{12}$, could also be measured. The approximate position of conductive member 14 relative to elongate shaft 12 may be determined by various reflective power signatures or profiles. Power signatures and profiles may be specific for each microwave antenna assembly.

In yet another embodiment of the present disclosure, the position of conductive member 14 is used to determine which type of energy the generator may supply. Radio frequency energy, delivered in either a monopolar or bipolar mode, is typically delivered while microwave antenna assembly 10 is in a first condition (i.e., during positioning of the microwave antenna assembly 10 in tissue) and when deployed or retracted between the first condition and the second condition. Radio frequency energy may be selectively supplied, in a bipolar mode, when microwave antenna assembly 10 is in the first condition and, in a monopolar mode, when deploying or retracting conductive member between the first condition and the second condition. Microwave energy may be delivered by microwave antenna "M" following formation of the microwave antenna "M" at the distal end of microwave antenna assembly 10.

Figure 5:
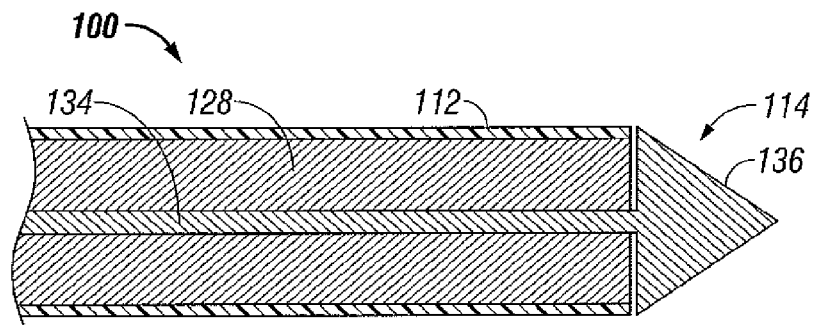
FIG. 5 is a schematic cross-sectional view of a distal portion of a microwave antenna assembly according to another embodiment of the present disclosure, shown in a first condition.
Figure 6:
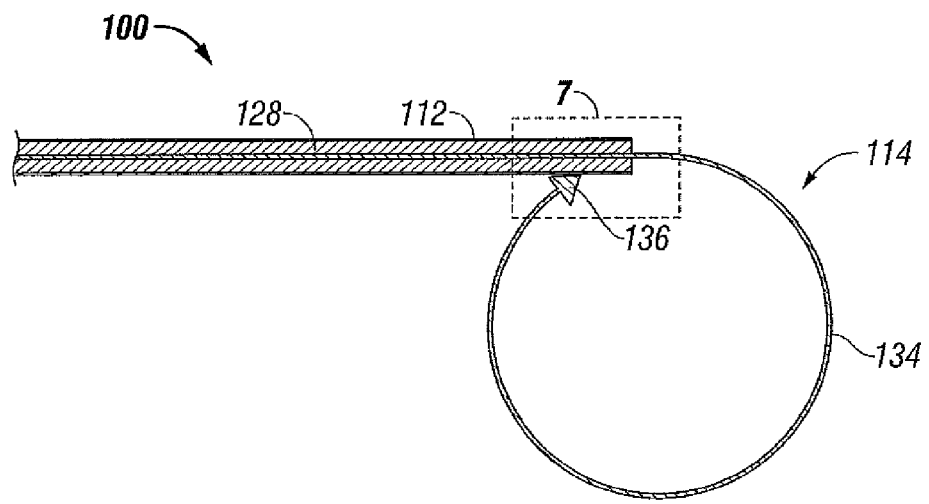
FIG. 6 is a schematic cross-sectional view of the distal portion of the microwave antenna assembly of FIG. 5, shown in a second condition.
Figure 7:
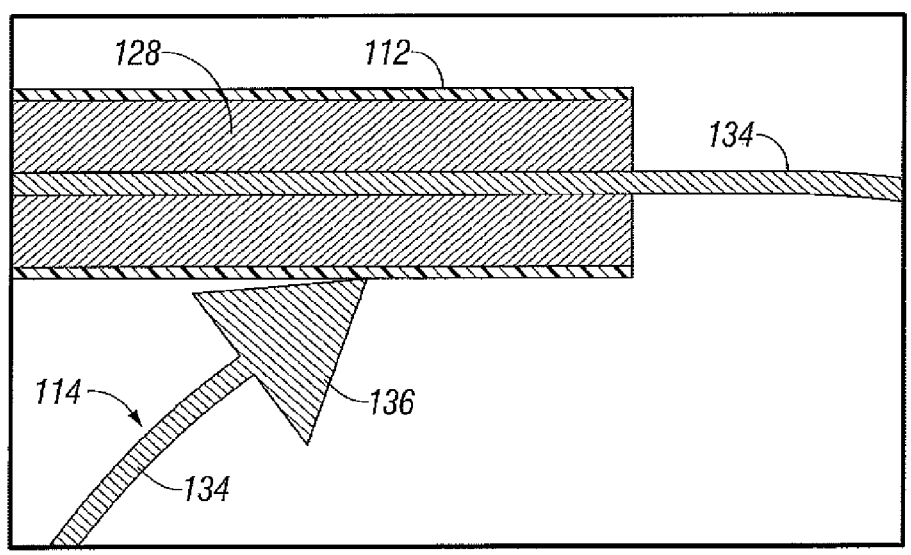
FIG. 7 is an enlarged view of the indicated area of detail of FIG. 6.

Turning now to FIGS. 5-7, another embodiment of a microwave antenna assembly in accordance with the present disclosure is designated as 100. Microwave antenna assembly 100 is substantially similar to microwave antenna assembly 10 and thus will only be described herein to the extent necessary to identify differences in construction and operation. Microwave antenna assembly 100 includes an elongate shaft 112 or outer conductor, a conductive member, or inner conductor 114, and a first dielectric material 128 interposed therebetween.

As depicted in FIG. 5, when microwave antenna assembly 100 is in a first condition first dielectric material 128 is disposed between elongate shaft 112 and conductive member 114. First dielectric material 128 and conductive member 114 are at least partially disposed within the lumen of elongate shaft 112. In the illustrated embodiment, a distal tip portion 136 of conductive member 114 is configured to penetrate tissue, and a distal tip portion of elongate shaft 112 is configured to not penetrate tissue (e.g., the distal tip portion of elongate shaft 112 may have a blunt or rounded profile to prevent it from penetrating tissue). When microwave antenna assembly 100 is in the first condition, distal tip portion 136 abuts the distal end of elongate shaft 112 with at least a portion of distal tip portion 136 extending distally beyond elongate shaft 112. A proximal section or surface of distal tip portion 136 is of similar size and cross section as a distal portion of elongate shaft 112 such that when in the first condition a smooth transition exists between distal tip portion 136 and elongate shaft 112. Distal tip portion 136 may engage first dielectric material 128 or the distal end of elongate shaft 112; however, the geometry (i.e., size and/or shape) of distal tip portion 136 impedes retraction of distal tip portion 136 into elongate shaft 112.

As depicted in FIG. 6, conductive member 114 is deployed from or extended from first dielectric material 128 when microwave antenna assembly 100 is in a second condition. In the second condition, distal tip portion 136 is spaced relative to the distal end of elongate shaft 112 and biased distal portion 134 of conductive member 114 is biased, flexed or bent to a pre-determined configuration.

As seen in FIG. 7, deployment of microwave antenna assembly 100 to the second condition places distal tip portion 136 in close proximity to the outer periphery or surface of elongate shaft 112 wherein resistive, capacitive and/or inductive contact exists between elongate shaft 112 and distal tip portion 136 or biased distal portion 134 of conductive member 114 and elongate shaft 112. It is desirable for the resistive, capacitive and/or inductive contact to be sufficient such that the contact improves the efficiency of the energy delivery, i.e. lower reflective power.

Resistive, capacitive and/or inductive contact between distal tip portion 136 and elongate shaft 112 improves the efficiency of energy delivery, i.e. lower reflective power. Microwave antenna assembly 100 may include a shorting-wire that connects distal portion of conductive member 114 to the distal portion of elongate shaft 112. The shorting-wire may attach to and run along distal portion 134 of the conductive member 114, deploy with the conductive member 114 to a second condition and provide the desired short-circuit between distal tip portion 136 and elongate shaft 112. Conductive member 114 may be hollow and the shorting-wire may be housed therewithin.

Figure 8:
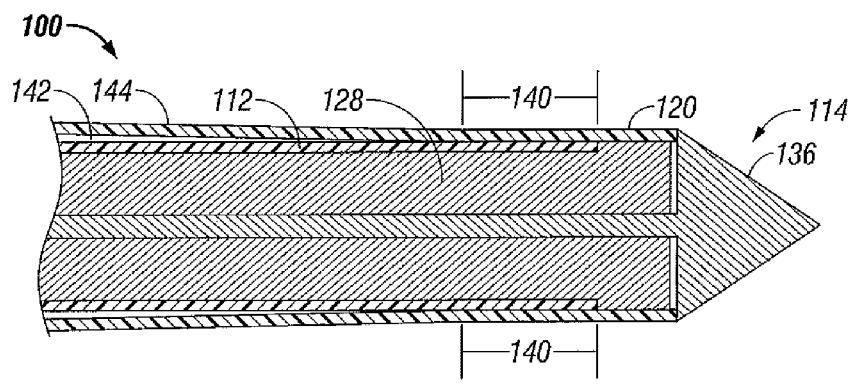
FIG. 8 is a schematic cross-sectional view of a distal portion of a microwave antenna assembly according to another embodiment of the present disclosure, shown in a first condition.

In the embodiment illustrated in FIG. 8, microwave antenna assembly 100 includes a cooling sheath 120 at least partially co-axially surrounding and extending over elongate member 112. Cooling sheath 120 may be formed of a conductive material, such as thin wall stainless steel. Elongate member 112 and cooling sheath 120 are connected to one another in a contact area 140 wherein cooling sheath 120 and elongate member 112 are shorted. Contact area 140 creates a fluid-tight seal between a cooling chamber 142 and an outside surface 144 of microwave antenna assembly 100. As seen in FIG. 8, a distal end of cooling sheath 120 is positioned distally of a distal end of elongate shaft 112. Cooling sheath 120 may, in some embodiments, only partially surround elongate member 112. In an embodiment, the distal end of elongate shaft 112 may extend past the distal end of cooling sheath 120 and engage tip portion 136 of conductive member 114. The engagement of distal tip portion 136 to conductive member and/or elongate member 112 may be used to signify non-deployment of the ring.

Referring now to FIGS. 3 and 8, cooling fluid supply 22 of cooling assembly 20, located on the proximal end of cooling sheath 21, may supply cooling fluid to distal end of cooling chamber 142. Cooling fluid may flow through cooling chamber 142 to cooling fluid return 24, located on proximal end of cooling sheath 21.

Microwave antenna assembly may include one or more temperature measuring device (not shown) such as a resistive temperature device (RTD) or a thermocouple. The temperature measuring device may measure one or more of the following: the temperature of the cooling fluid at one or more locations within cooling chamber 142; the temperature of one or more of the components of the microwave antenna assembly; or the temperature of patient tissue.

With continued reference to FIG. 8, when microwave antenna assembly 100 is in the first condition, distal tip portion 136 of conductive member 114 engages the distal portion of cooling sheath 120 and/or the distal portion of elongate shaft 112 or a portion of first dielectric material that extends beyond cooling sheath 120 and elongate shaft 112 (if cooling sheath 120 does not extend beyond distal end of elongate shaft 112). Irrespective of which element distal tip portion 136 engages, a smooth transition is formed between an exterior surface of distal tip portion 136 and the adjacent abutting member in order to facilitate tissue penetration.

Figure 8A:
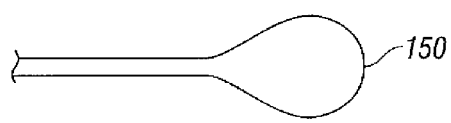
FIGS. 8A-8F illustrate alternate embodiments of distal portions of conductive members of the microwave assemblies disclosed herein.
Figure 8B:
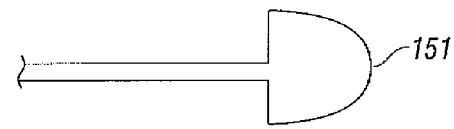
Figure 8C:
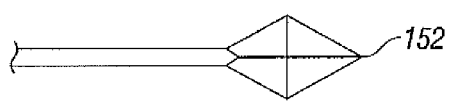
Figure 8D:
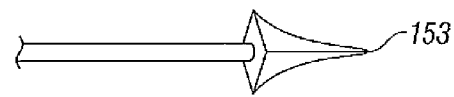
Figure 8E:
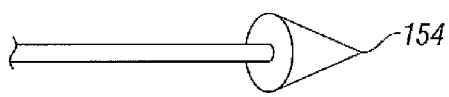
Figure 8F:
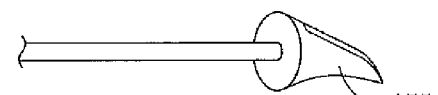

As mentioned above the distal tip portion is configured to define a pathway through the tissue during tissue penetration and may have any suitable geometry. Referring now to FIGS. 8A-8F, various geometries for distal tip portions, used to define a pathway through the tissue, are illustrated as 150-155, respectively. FIGS. 8A and 8B depict geometries of distal tip portion 150, 151, respectively, with smooth surfaces adapted to create a pathway through the tissue with the application of electrical energy, e.g., tear drop (FIG. 8A), hemispherical (FIG. 8B). FIGS. 8C and 8D depict geometries with sharp or piercing distal tips adapted to create a pathway when applied with mechanical force. Other geometries are suitable provided the distal edge of the distal tip portion forms a sharp feature as the leading edge for introducing the device to the desired location. If the pathway is created with the application of electrical and mechanical energy any of the geometries illustrated in FIGS. 8A-8F, as well as other geometries, may be utilized. The distal portion of the first dielectric material 128 is adapted to conform to the geometry of the proximal surface of the distal tip portion 150, 151, 152, 153, 154, 155 depicted in FIGS. 8-8F, respectively.

Figure 9:
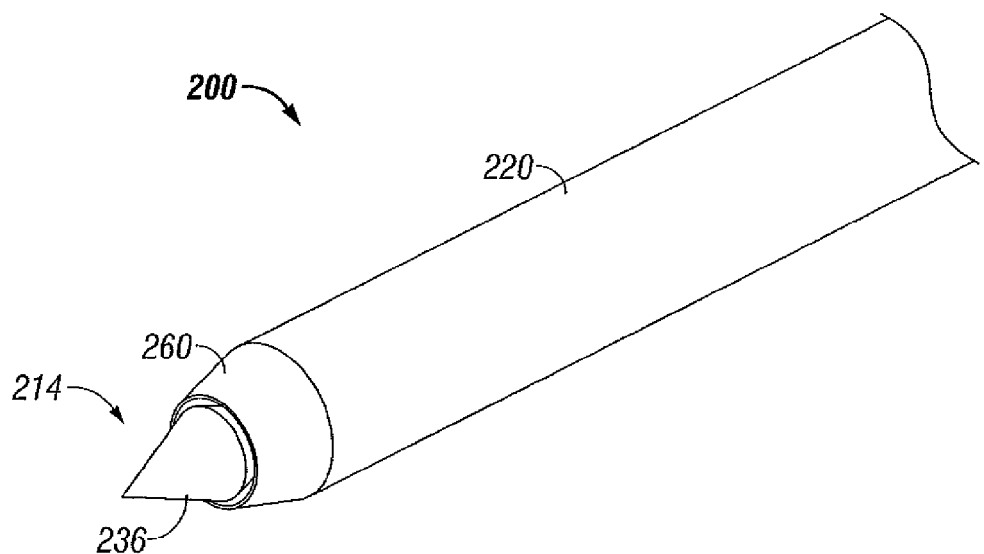
FIG. 9 is a schematic distal perspective view of a microwave antenna assembly according to a further embodiment of the present disclosure, shown in a first condition.
Figure 10:
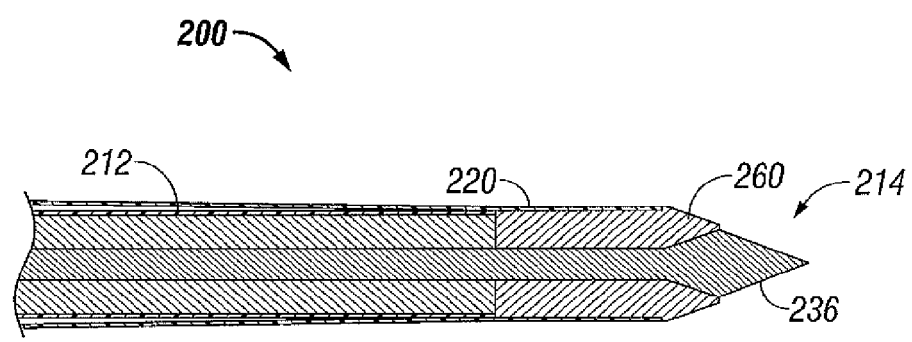
FIG. 10 is a longitudinal cross-sectional view of the distal portion of the microwave assembly of FIG. 9.
Figure 11:
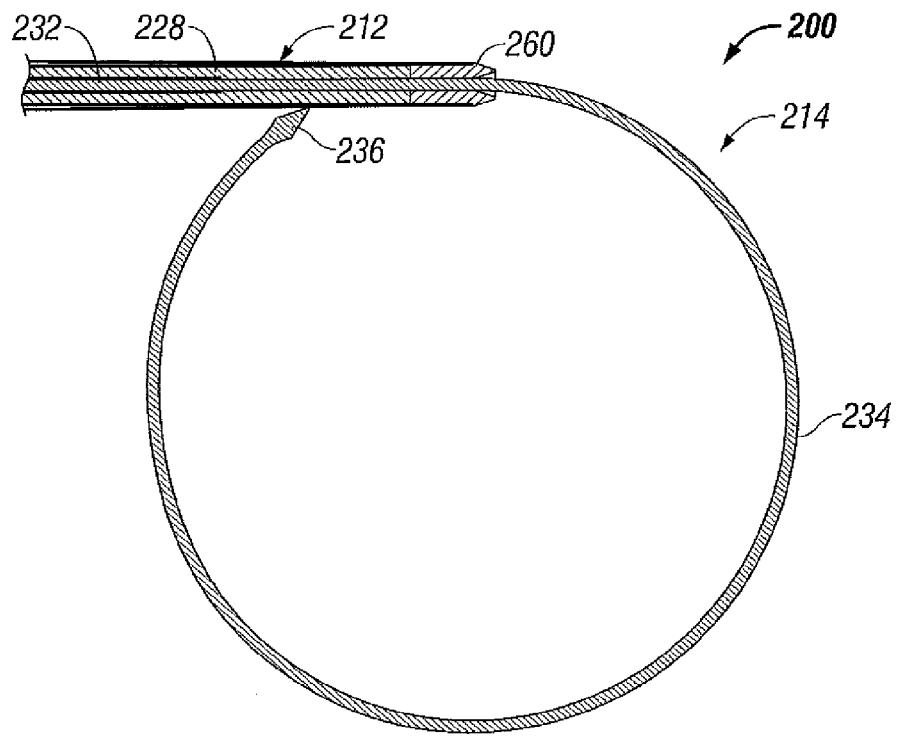
FIG. 11 is a longitudinal cross-sectional view of the distal portion of the microwave antenna assembly of FIGS. 9 and 10, shown in a second condition.

Turning now to FIGS. 9-11, a microwave antenna assembly according to another embodiment of the present disclosure is shown as 200. Microwave antenna assembly 200 includes a transition member 260 disposed at the distal end of elongate shaft 212 and at least partially surrounding conductive member 214. Transition member 260 includes a distal tapered surface 260 that creates a smooth transition with elongate shaft 212 to facilitate tissue penetration. As seen in FIG. 10, transition member 260 is secured to the distal end of elongate shaft 212 by cooling sheath 220 extending at least partially over elongate shaft 212 and transition member 260.

Transition member 260 strengthens the distal portion of the microwave antenna assembly 200 for tissue penetration and acts as a dielectric electrically insulating distal tip portion 236 from cooling sheath 220 and elongate shaft 212. Transition member 260 also allows the maximum cross sectional area of the distal tip portion 236 to be reduced to a value less than the cross sectional area of elongate shaft 212 or of cooling sheath 220. The reduced maximum cross-sectional area of the distal tip portion 236 creates a smaller pathway in tissue and requires less force to penetrate tissue when deploying between a first condition and a second condition.

Figure 12:
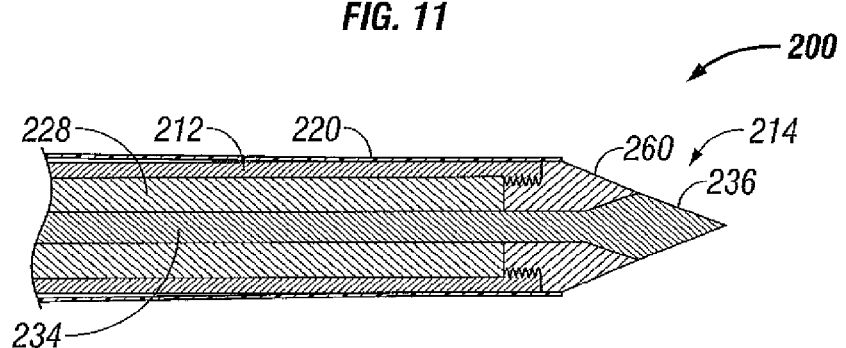
FIG. 12 is a longitudinal cross-sectional view of a distal portion of a microwave antenna assembly according to an alternate embodiment of the present disclosure, shown in a first condition.

With reference to FIG. 12, transition member 260 of microwave antenna assembly 200 engages both elongate shaft 212 and cooling sheath 220. A press fit engagement is utilized to mate transition member 260 to cooling sheath 220 while a threaded engagement is used to mate transition member 260 to elongate shaft 212.

Figure 13:
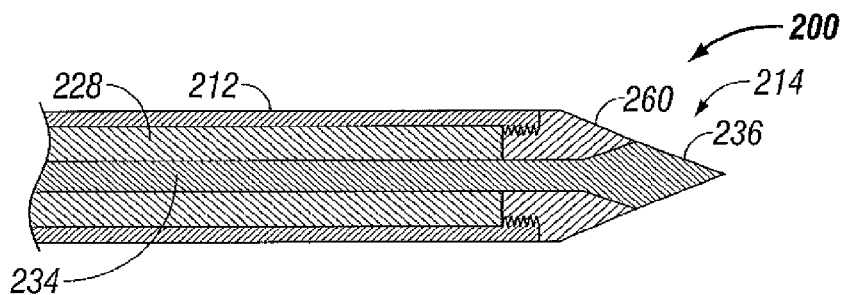
FIG. 13 is a longitudinal cross-sectional view of a distal portion of a microwave antenna assembly according to an alternate embodiment of the present disclosure, shown in a first condition.

With reference to FIG. 13, cooling sheath 220 has been removed and transition member 260 is mated with elongate shaft 212 via a threaded engagement, although other securing means and methods can be used. Distal tip portion 236, elongate shaft 212 and transition member 260 create a smooth transition between one another in order to facilitate tissue penetration while microwave antenna assembly 200 is in a first condition. Various other suitable methods may be used for mating elements to one another.

Figure 15:
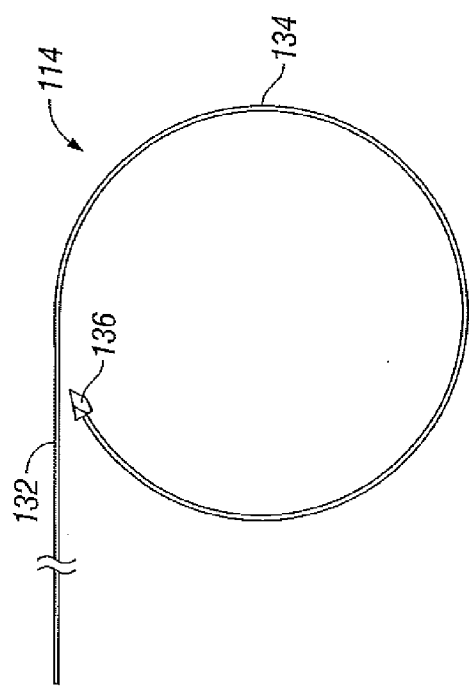
FIG. 15 is a schematic cross-sectional view of a microwave antenna assembly according to another embodiment of the present disclosure with the conductive member of FIG. 14, shown partially deployed.

Referring now to FIGS. 14 and 15, as described above conductive member 114 includes a proximal portion 132, a biased distal portion 134 and a distal tip portion 136. When microwave antenna assembly 100 is substantially in a first condition, as seen in FIG. 14, biased distal portion 134 and proximal portion 132 are substantially retracted within elongate shaft 112 and are surrounded by first dielectric material 128 while distal tip portion 136 is located distal of elongate shaft 112. When microwave antenna assembly 100 is in a second condition, as seen in FIG. 15, the portion of conductive member 114 exposed to tissue includes biased distal portion 134 and distal tip portion 136. If radio frequency energy is utilized to define a pathway during deployment or retraction, distal portion 134 and distal tip portion 136 deliver radio frequency energy to tissue. While the main pathway will be created by the curvilinear movement of distal tip portion 136 through tissue, lateral movement of the deployed portion is possible since the entire deployed portion is energized with radio frequency energy.

Figure 17:
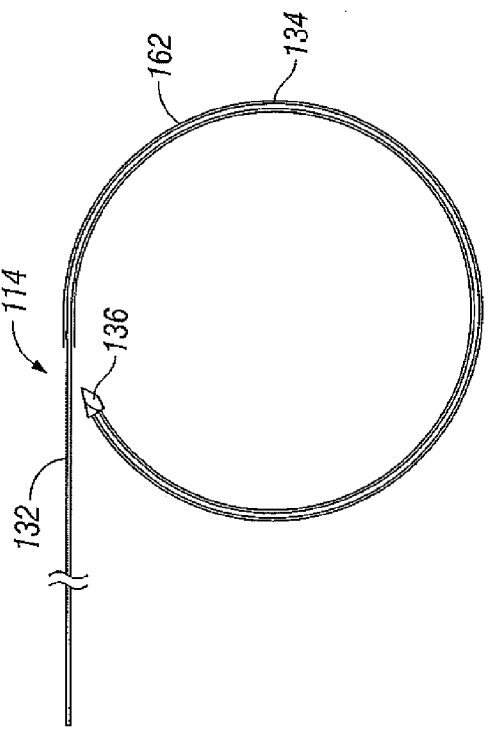
FIG. 17 is a schematic cross-sectional view of a microwave antenna assembly according to another embodiment of the present disclosure with the conductive member of FIG. 16, shown partially deployed.

Referring now to FIGS. 16 and 17, microwave antenna assembly 100 includes a second dielectric material 162 disposed between elongate shaft 112 and conductive member 114. Second dielectric material 162 covers at least a portion of conductive member 114 including a substantial amount of the length of biased distal portion 134. Second dielectric material 162 may be a PTFE shrink with a non-stick outer surface having a high temperature profile, although other suitable dielectrics may be used. The various properties of second dielectric material 162, such as material type and thickness, can be adjusted to better match the antenna assembly to tissue. Second dielectric material 162 defines the outer diameter of biased distal portion 134 of conductive member 114. In one embodiment, the outer diameter of second dielectric material 162 should form a smooth transition with the proximal end of distal tip portion 136 to facilitate movement of conductive member in tissue between a first condition and a second condition. The outer diameter of the second dielectric material 162 is also dimensioned to conform with the inner diameter of elongate shaft 112 such that when microwave antenna assembly 100 is in a first condition biased distal portion 134 and second dielectric material 162 are retracted within the lumen of elongate shaft 112.

As seen in FIG. 17, when microwave antenna assembly 100 is in a second condition, the portion of conductive member 114 deployed from microwave antenna assembly 100 includes distal tip portion 136, biased distal portion 134 and second dielectric material 162 covering biased distal portion 134. If radio frequency energy is utilized, when deploying conductive member between a first condition and a second condition, distal tip portion 136 will deliver radio frequency energy to tissue. The pathway through the tissue is created by the curvilinear movement of the distal tip portion 136 through the tissue and the energy delivered is concentrated at the distal end of distal tip portion 136.

The outer surface of second dielectric material 162 may also be coated. The coating is a suitable lubricious substance to aid in the movement of conductive member 114 between a first condition and a second condition as well as to aid in preventing tissue from sticking to the outer surface thereof. The coating itself may be made from suitable conventional materials, e.g., polymers, etc.

Yet another embodiment of a microwave antenna assembly 300, in accordance with the present disclosure, is illustrated in FIGS. 18-22. In the present embodiment, microwave antenna assembly 300 includes an introducer 316, a conductive member 314 and an elongate shaft 312 slidably disposed within introducer 316, a first dielectric material 328 interposed between conductive member 314 and elongate shaft 312, a second dielectric material 362 interposed between conductive member 314 and introducer 316 at a location distal of first dielectric material 328, and a cooling sheath 320. Conductive member 314 includes a distal tip portion 336 configured to engage the distal portion of introducer 316 and has a geometry such that distal tip portion 336 impedes retraction thereof into a lumen 316a of introducer 316. Second dielectric material 362 substantially covers biased distal portion 334 of conductive member 314. The elongate shaft 312, cooling sheath 320 and first dielectric material 328 are positioned within lumen 316a of introducer 316. It is envisioned that first dielectric material 362 and second dielectric material 328 may be the same or may be formed of the same material.

As seen in FIGS. 18 and 19, distal tip portion 336 of conductive member 314 forms a smooth transition with introducer 316 such that the distal end of the microwave antenna assembly 300 is adapted for penetrating tissue and to facilitate insertion of microwave antenna assembly 300 into tissue.

Figure 20:
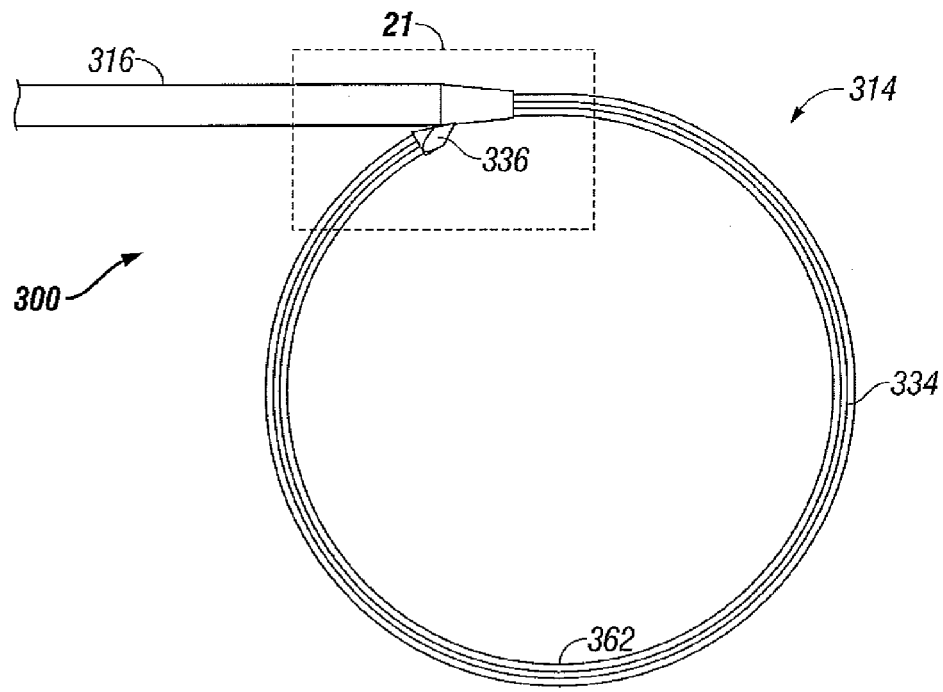
FIG. 20 is a side elevational view of the microwave antenna assembly of FIGS. 18 and 19, shown in a second condition.
Figure 21:
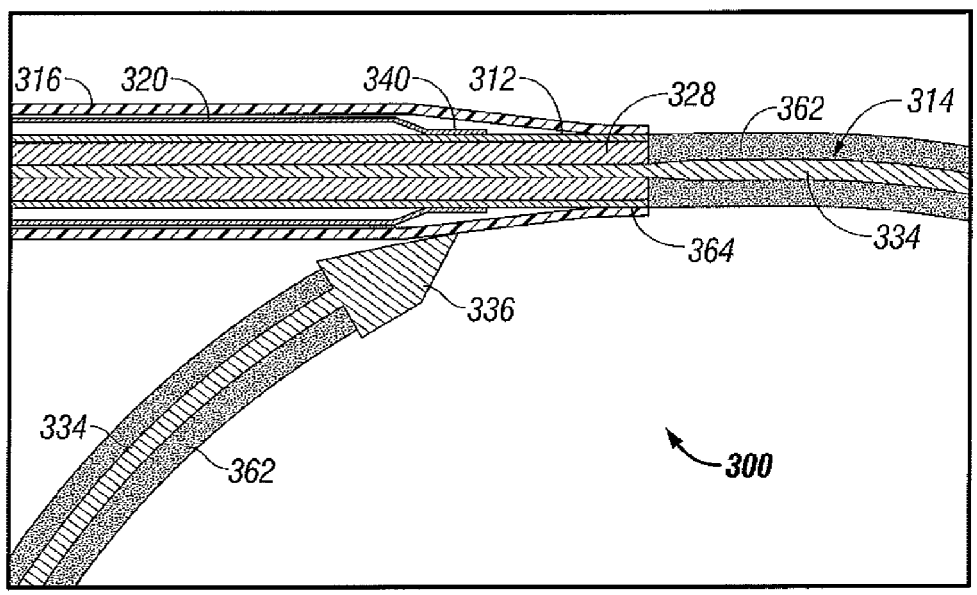
FIG. 21 is an enlarged longitudinal cross-sectional view of the indicated area of detail of the microwave antenna assembly of FIG. 20.

As seen in FIGS. 20 and 21, microwave antenna assembly 300 has been deployed to a second condition. When microwave antenna assembly 300 is deployed to the second condition, elongate shaft 312, cooling sheath 320 and first dielectric material 328 are repositioned and/or advanced from a proximal end portion of introducer 316 to a distal end portion of introducer 316. In particular, elongate shaft 312 is advanced an amount sufficient to contact the distal end portion of introducer 316 at or near a distal tip 364 thereof to form a resistive, capacitive and/or inductive connection therebetween. As discussed in the earlier embodiments, elongate shaft 312 contacts cooling sheath 320 and forms a resistive, capacitive and/or inductive connection at a contact area 340. When microwave antenna assembly 300 is in the second condition distal end of conductive member 314 is spaced a distance relative to a distal end of introducer 316 and bends around such that distal tip portion 336 is in close proximity to an exterior surface of introducer 316. Distal tip portion 336 of conductive member 314 may have or be in resistive, capacitive and/or inductive contact with introducer 316.

In another embodiment of the present disclosure, cooling sheath 320 may be incorporated into introducer 316 and conductive member 314, elongate shaft 312 and first and second dielectric materials 328, 362 are slidably positioned therewithin.

Figure 22:
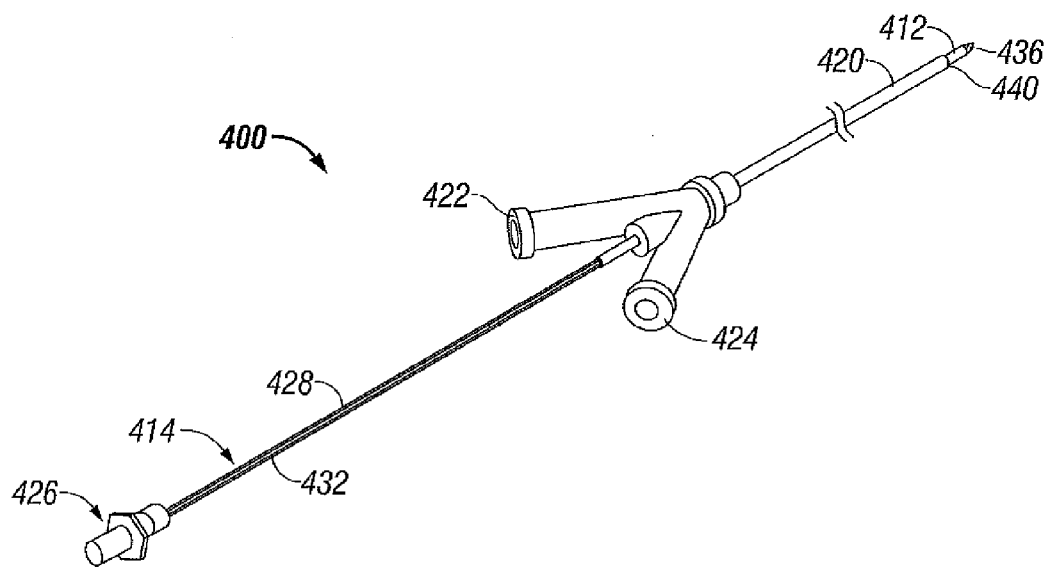
FIG. 22 is a schematic perspective view of a microwave antenna assembly according to yet another embodiment of the present disclosure, shown in a first condition.
Figure 23:
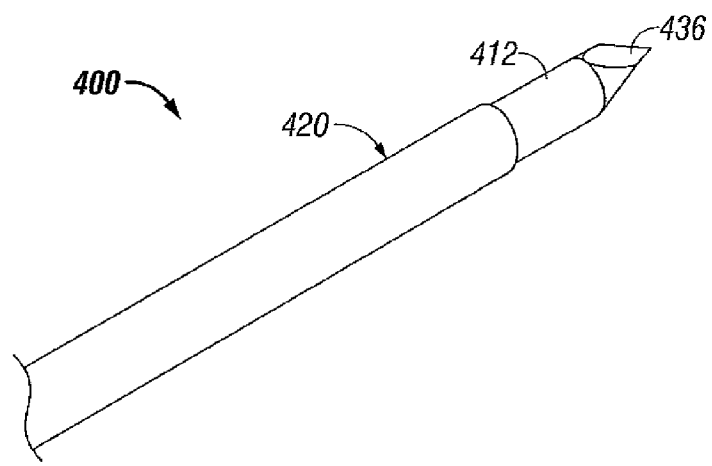
FIG. 23 is an enlarged perspective view of the distal portion of the microwave antenna assembly of FIG. 22.
Figure 24:
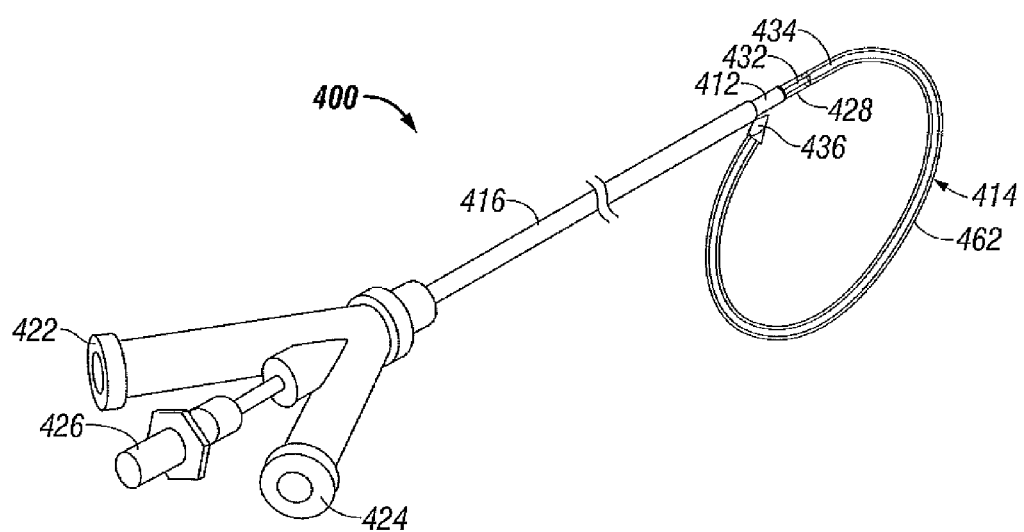
FIG. 24 is a perspective view of the microwave antenna assembly of FIG. 22, shown in a second condition.

Another embodiment of microwave antenna assembly 400, in accordance with the present disclosure, is illustrated in FIGS. 22-24. In the present embodiment, microwave antenna assembly 400 includes a conductive member 414, a first dielectric material 428 covering at least a portion of a proximal portion 432 of conductive member 414, a second dielectric material 462 covering a biased distal portion 434 of conductive member 414, and a connector 426 connected to the proximal end of conductive member 414. A distal tip portion 436 of conductive member 414 is configured to engage a distal end of elongate shaft 412.

Microwave antenna assembly 400 further includes a cooling sheath 420 extending over elongate shaft 412 and engaging elongate shaft 412 at contact area 440. Cooling sheath 420 engages elongate shaft 412 in such a manner so as to form a water-tight seal therebetween. Cooling fluid, supplied to the proximal end of a cooling chamber, defined between cooling sheath 420 and elongate shaft 412, through a cooling fluid supply 422, flows from the proximal end of the cooling chamber to the distal end and returns through the cooling chamber to exit microwave antenna assembly 400 through a cooling fluid return 424.

As seen in FIG. 23, when microwave antenna assembly 400 is in a first condition, distal tip portion 436 forms a smooth transition with elongate shaft 412 to facilitate tissue penetration. The geometry of distal tip portion 436 is such that retraction of distal tip portion 436 into elongate shaft 412 is prevented. Elongate shaft 412 may also form a smooth transition with cooling sheath 420.

As seen in FIG. 24, when microwave antenna assembly 400 is in a second condition, distal tip portion 436 of conductive member 414 is spaced a relative distance to the distal end of elongate shaft 412, proximal portion 432 is substantially disposed within the lumen of elongate shaft 412, and distal biased portion 434, covered by second dielectric material 462, projects out from the distal end of elongate shaft 412. When distal tip portion 436 and distal biased portion 434 are deployed to the second condition a microwave antenna is formed. The distal end of conductive member 414 may form a resistive, capacitive and/or inductive connection with elongate shaft 412, as discussed supra.

The applications of the microwave antenna assemblies and methods of using the assemblies discussed above are not limited to microwave antennas used for hyperthermic, ablation, and coagulation treatments but may include any number of further microwave antenna applications. Modification of the above-described assemblies and methods for using the same, and variations of aspects of the disclosure that are obvious to those of skill in the art are intended to be within the scope of the claims.

What is claimed is:

1. A microwave antenna assembly comprising:
   an elongate shaft having a lumen defined therein;
   a conductive member partially disposed within the lumen of the elongate shaft, the conductive member including a geometry at a distal end thereof configured to penetrate tissue;
   a first dielectric material disposed between the elongate shaft and at least a portion of the conductive member; and
   a second dielectric material that covers at least a portion of the conductive member;
   wherein at least one of the elongate shaft, the conductive member, the first dielectric material and the second dielectric material being configured to selectively deploy relative to a distal end of an introducer from a first condition wherein a distal end of the conductive member at least partially abuts a distal end of the introducer to a second condition wherein the distal end of the conductive member is spaced relative to the distal end of the introducer, and
   wherein the geometry at the distal end of the conductive member has a diameter larger than a diameter of at least one of a distal portion of the introducer or a distal portion of the lumen of the elongate shaft.

2. The microwave antenna assembly according to claim 1, wherein the distal end of the conductive member is distal to the introducer.

3. The microwave antenna assembly according to claim 2, wherein the conductive member biases to a pre-determined configuration when in the second condition.

4. The microwave antenna assembly according to claim 3, wherein the geometry at the distal end of the conductive member impedes retraction of the distal end of the conductive member into the lumen of the elongate shaft.

5. The microwave antenna assembly according to claim 4, wherein the geometry at the distal end of the conductive member engages a distal portion of the elongate shaft.

6. The microwave antenna assembly according to claim 5, wherein the distal end of the conductive member defines a pathway in tissue during tissue penetration.

7. The microwave antenna assembly according to claim 6, wherein the pathway is created mechanically.

8. The microwave antenna assembly according to claim 7, wherein the pathway is defined by virtue of the mechanical geometry of the conductive member and the application of energy to tissue.

9. The microwave antenna assembly according to claim 8, wherein the conductive member is adapted to connect to an energy source which supplies at least one of radio frequency energy and microwave energy.

10. The microwave antenna assembly according to claim 9, wherein the conductive member is configured to supply radio frequency energy when disposed in the first condition.

11. The microwave antenna assembly according to claim 9, wherein the conductive member is configured to supply microwave energy when in the second condition.

12. The microwave antenna assembly according to claim 11, wherein the conductive member connects with the elongate shaft when in the second condition.

13. The microwave antenna assembly according to claim 9, wherein the conductive member is configured to supply radio frequency energy when the conductive member is disposed in the first condition and microwave energy when the conductive member is in the second condition.

14. The microwave antenna assembly according to claim 13, further comprising at least one sensor for determining the relative position of the conductive member.

15. The microwave antenna assembly according to claim 14, further comprising a switch for activating one of RF energy and microwave energy.

16. The microwave antenna assembly according to claim 3, wherein the geometry at the distal end of the conductive member impedes retraction of the distal end of the conductive member into the introducer.

17. The microwave antenna assembly according to claim 16, wherein the geometry at the distal end of the conductive member engages the distal end of the introducer.

18. The microwave antenna assembly according to claim 1, further comprising a cooling sheath at least partially surrounding the conductive member, the cooling sheath adapted to connect to a coolant source.

* * * * *